(12) United States Patent
Nahshon

(10) Patent No.: US 10,231,811 B2
(45) Date of Patent: Mar. 19, 2019

(54) DEVICE AND METHOD FOR TEETH TREATMENT

(71) Applicant: BRIGHTTONIX MEDICAL LTD., Yokneam Illit (IL)

(72) Inventor: Genady Nahshon, Netanya (IL)

(73) Assignee: BRIGHTTONIX MEDICAL LTD., Yokneam Illit (IL)

( * ) Notice: Subject to any disclaimer, the term of this patent is extended or adjusted under 35 U.S.C. 154(b) by 0 days.

(21) Appl. No.: 15/302,165

(22) PCT Filed: Sep. 8, 2015

(86) PCT No.: PCT/IL2015/050912
§ 371 (c)(1),
(2) Date: Oct. 6, 2016

(87) PCT Pub. No.: WO2016/051400
PCT Pub. Date: Apr. 7, 2016

(65) Prior Publication Data
US 2017/0027675 A1 Feb. 2, 2017

Related U.S. Application Data

(60) Provisional application No. 62/059,879, filed on Oct. 4, 2014, provisional application No. 62/085,277, filed on Nov. 27, 2014.

(51) Int. Cl.
*A61C 1/00* (2006.01)
*A61C 19/06* (2006.01)
(Continued)

(52) U.S. Cl.
CPC .......... *A61C 19/066* (2013.01); *A61C 19/063* (2013.01); *A61N 1/0548* (2013.01);
(Continued)

(58) Field of Classification Search
None
See application file for complete search history.

(56) References Cited

U.S. PATENT DOCUMENTS 3,502,076 A * 3/1970 Bertolini .............. A61C 19/063
604/20
6,174,164 B1 * 1/2001 Masjedi ................ A61C 17/00
433/215
(Continued)

FOREIGN PATENT DOCUMENTS

EP 1 525 857 B1 2/2007
JP 2012-110500 A 6/2012
WO 2015/022680 A1 2/2015

OTHER PUBLICATIONS

Supplementary European Search Report for EP 15847080, dated Jan. 2, 2017.
(Continued)

*Primary Examiner* — Nicholas Lucchesi
*Assistant Examiner* — Shannel Wright
(74) *Attorney, Agent, or Firm* — Browdy and Neimark, P.L.L.C.

(57) ABSTRACT

A teeth whitening device and method are presented. The teeth whitening device is configured for controllable application of AC activation signal to a regular toothpaste contacting teeth under treatment, thereby providing relatively short and effective whitening process while avoiding a need for strong oxidizing agents.

14 Claims, 3 Drawing Sheets

(51) Int. Cl.
*A61N 1/32* (2006.01)
*A61N 1/05* (2006.01)
*A61M 37/00* (2006.01)

(52) U.S. Cl.
CPC ............ *A61N 1/325* (2013.01); *A61C 1/0015* (2013.01); *A61M 2037/0007* (2013.01)

(56) References Cited

U.S. PATENT DOCUMENTS

| | | | | |
|---|---|---|---|---|
| 7,422,598 | B2* | 9/2008 | Altshuler | A46B 15/0002 607/88 |
| 7,775,795 | B2* | 8/2010 | Khawaled | A61C 19/066 433/214 |
| 8,660,669 | B2* | 2/2014 | Nemeh | A61C 19/063 433/216 |
| 8,663,607 | B2* | 3/2014 | Monzyk | A61K 31/295 424/49 |
| 2005/0064370 | A1* | 3/2005 | Duret | A61C 19/066 433/215 |
| 2005/0074723 | A1* | 4/2005 | Ostler | A61C 17/20 433/216 |
| 2005/0202363 | A1* | 9/2005 | Osterwalder | A61C 9/0006 433/29 |
| 2007/0160958 | A1* | 7/2007 | Belikov | A61C 19/063 433/215 |
| 2007/0212665 | A1* | 9/2007 | Jimenez | A61C 17/16 433/215 |
| 2008/0003540 | A1* | 1/2008 | Khawaled | A61C 19/066 433/215 |
| 2008/0060148 | A1* | 3/2008 | Pinyayev | A61B 5/0088 15/22.1 |
| 2008/0199830 | A1* | 8/2008 | Fontenot | A46B 5/0012 433/215 |
| 2008/0233541 | A1* | 9/2008 | De Vreese | A61C 19/066 433/216 |
| 2008/0311545 | A1* | 12/2008 | Ostler | A61C 17/20 433/216 |
| 2010/0178630 | A1* | 7/2010 | Novak | A61C 19/063 433/37 |
| 2010/0209515 | A1* | 8/2010 | Chantalat | A61K 33/30 424/490 |
| 2011/0076636 | A1* | 3/2011 | Wolff | A61C 19/063 433/27 |
| 2012/0156648 | A1* | 6/2012 | Kaufman | A61C 19/066 433/215 |
| 2012/0251971 | A1* | 10/2012 | Fish | A46B 15/0002 433/27 |
| 2012/0315596 | A1* | 12/2012 | Gan | A61C 19/066 433/32 |
| 2013/0042876 | A1* | 2/2013 | Hermanson | A61F 5/566 128/848 |
| 2014/0093832 | A1* | 4/2014 | Nemeh | A61C 19/063 433/1 |
| 2014/0162206 | A1* | 6/2014 | Ivanoff | A61N 1/0428 433/32 |
| 2015/0044628 | A1* | 2/2015 | Flyash | A61C 19/066 433/27 |
| 2016/0361149 | A1* | 12/2016 | Otsuka | A61C 19/066 |
| 2017/0197071 | A1* | 7/2017 | Gottenbos | A61C 15/047 |

OTHER PUBLICATIONS

International Search Report for PCT/IL2015/050912, dated Dec. 21, 2015.
Written Opinion for PCT/IL2015/050912, dated Dec. 21, 2015.

* cited by examiner

DEVICE AND METHOD FOR TEETH TREATMENT

TECHNOLOGICAL FIELD

The present invention is generally in the field of aesthetic medical devices and cosmetic devices, and relates particularly to dental treatment and teeth whitening device and method.

BACKGROUND

Tooth discoloration is a known problem existing in almost every country and population. There are different reasons why the teeth could become stained. For example, the teeth may become stained by coffee, tea or red wine drinking, or by the use of tobacco products, or by eating a food or consuming water with a high mineral content, or using certain antibiotics.

In addition to the healthy problems associated with the coloration of teeth cased by the above, stained or discolored teeth could become a social problem, since pleasant external appearance is important in every society. In recent years, techniques have been developed for teeth whitening or bleaching. White teeth are believed to improve aesthetic appearance of a person.

Teeth bleaching or teeth whitening procedure as referred to in the current disclosure is a process that removes the colored stains from the teeth to reveal the natural white teeth color.

Some of the known methods and products for teeth whitening or bleaching could be used or applied by professional personnel, and some other techniques could be used by a casual user in residential environment. Most of the products for use in a residential environment contain strong oxidizers that contain or synthesize hydrogen peroxide ($H_2O_2$) known to be a bleaching agent. Products for use in residential environment are typically less effective than products and methods used by professional personnel or professional dental bleaching services providers. Teeth whitening treatment performed in residential environment and capable of providing results similar or close to the ones provided by professional dental bleaching services providers usually take significantly more time. The known methods also require use of dedicated materials designed for the specific methods. These materials carry a certain cost.

U.S. Pat. No. 7,775,795 to Khawaled discloses an electrochemical method and device for treating teeth. According to this method, metal salt solution and ionizable substance are applied to teeth, and electric current flow is applied so as to ionize the ionizable substance. The electrochemical device includes an applicator for applying a substance to teeth, having a first end and a second end, a first electrode attached to first end of applicator, second electrode attached to second end of applicator, wherein first electrode and second electrode are configured for current flow through applicator, and an ionizable substance for placement within applicator. The ionizable substance is configured for ionization upon application of current flow through the substance. The electrochemical teeth whitening procedure includes application of metal salt solution and an oxidizing agent such that when electric current flow is applied the oxidizing agent is activated and reduced for effecting whitening of the teeth.

European Patent 1 525 857 B1 to Tessarotto discloses a device for treating teeth and/or oral mucosal tissue by electrolysis. The dental device has positive and negative electrodes, and an electrolytically conductive composition is applied to the dental device. The conductive composition contains water and an electrolyte and is preferably in thickened form. The positive and negative electrodes are spaced apart and are preferably placed on a front and hack portion of the dental device, respectively. The conductive composition is placed in the device between the positive and negative electrodes. Once power is activated, an electric current is sent to the electrodes and the conductive composition generates one or more oxidizing agents which whiten the user's teeth. Additionally, the oxidizing agents eliminate harmful bacteria in the; regions around the teeth.

Known conventional teeth whitening methods typically utilize either a traditional tray or an adhesive strip to apply the whitening material to the teeth. Naturally, a part of the whitening material escapes from the tray or is squeezed on the gingival tissue in the region adjacent to the teeth to be whitened. That squeezed on the gingival tissue whitening material causes a burning sensation to that tissue. Because of this, prior to applying whitening or bleaching to the teeth it is necessary to isolate and protect the patient's gums that could be exposed to the whitening material. This is usually done by including in the tray construction a rubber dam preventing escape of the whitening material or covering the sensitive gingival region by a type of protective material that could be a lacquer.

The results of teeth whitening procedure typically do not change permanently the teeth color and has to be periodically repeated depending on the life style and food consumed of an individual.

GENERAL DESCRIPTION

There is a need in the art to provide a novel teeth whitening technique which is effective, safe, easy to apply, enabling accessible way for home, as well as professional use (including dental and cosmetic clinics such as spa).

To this end, the present invention provides for a novel approach for teeth whitening, which may be implemented by a simple yet strongly effective device and method, which is suitable for use in personal and professional teeth whitening treatment. The technique of the present invention provides the treatment results at the level of professional treatment while saving time and money. Additionally, as the treatment can be made by the individual at home, it can be repeated as needed while saving the effort of repeatedly visiting professional clinics.

The present invention utilizes a whitening substance based on a regular toothpaste together with application of a customized alternating electric field/current (AC) to the toothpaste and/or teeth (generally, at least one tooth).

It should be noted that for the purposes of the present application the term "regular toothpaste" refers to a toothpaste having no oxidizing agents (such as used in conventional teeth whitening procedures), and may be any known suitable commercially available toothpaste, but preferably of the type containing teeth whitening agents and/or hyaluronic acid. This makes the teeth whitening procedure more safe and simple.

Some specific hut not limiting examples of the suitable toothpaste include the following: Aquafresh MULTI-ACTION WHITENING; Oral-B Complete Mouthwash+Whitening; Colgate MAX WHITE ONE; Colgate OPTIC WHITE, Colgate Sensitive Whitening, Dr. John's Formula Toothpaste Gel. As stated above, these are all trade names for commercially available toothpaste, in particular containing whitening agents and/or hyaluronic acid.

Also, it should be noted that in the description below the terms "regular toothpaste", "whitening toothpaste", "whitening substance" and "whitening material" are used interchangeably, all relating to a whitening substance, e.g. regular toothpaste, without strong oxidizing agents (such as conventionally used hydrogen peroxide). In some embodiments of the invention the "regular toothpaste" is modified to include ferromagnetic particles (e.g. nanostructures) embedded therein and/or hyaluronic acid. Thus, the term "whitening substance based on a regular toothpaste" refers to the regular toothpaste itself or the regular toothpaste with the embedded magnetic particles and/or hyaluronic acid.

It should be noted that for the purposes of the present invention, the term "electric field" should be interpreted broadly covering also magnetic and electromagnetic field.

The inventor has found that the use of application of AC electric field having certain time and frequency pattern (function of time and/or frequency) to a regular toothpaste during a treatments session (i.e. when the whitening substance is in contact with teeth) provides for remarkable improvement of several shade degrees in accordance with the common shading grading, while in a relatively short duration of the treatment session (in comparison to the common professional practice) and without a need for strong oxidizing agents in the whitening substance. Preferably, the AC field application during the treatment session is continuous, but generally a proper pulsed mode can be used.

It should further be noted that alternating current (AC) or alternating electric field, as used for the purposes of the present application, refers to an electric current/field that reverses its polarity at regularly or irregularly recurring intervals of time, and which thus has alternatively positive and negative values. The shape/profile of the alternating current/field could be of a sinusoidal, rectangular, triangular, saw tooth or any other shape.

Thus, according to a first broad aspect of the invention, there is provided a device for use in teeth whitening procedure, the device comprising a treatment tray and an electric power source. The tray comprises an electrode unit (including at least one electrode) which is in electric connection with the electric power source. The tray is configured to be applied to the teeth and to receive therein a whitening substance to contact the teeth (generally at least one tooth, as the case may be), while the substance is either in contact with the electrode unit or located within an electric field region created by the electrode unit. The power source unit is configured to generate an alternating electric field in the form of a predetermined activation function, being a time frequency function, and maintain the application of the alternating, electric field for a predetermined duration (treatment session). Thus, during the treatment session such AC field activation function is continuously applied to the whitening substance, via said electrode unit, thereby causing improvement of white shade grade of the teeth being in contact with the whitening substance.

The device of the invention may be used as a medical or cosmetic device (either for professional or home use).

The term "electric power source unit" refers to a voltage or current source, as well as electromagnetic field source.

Preferably, the frequency (or frequencies) of the AC electric field is/are in a relatively high frequency range, at least a few hundreds of kHz, e.g. at least 300 kHz, up to a few tens of MHz, e.g. 40 MHz. The range may for example be from 1.0 MHz to 10 MHz.

In a preferred embodiment, the whitening substance is a regular commercially available whitening toothpaste. Generally, the whitening substance may be any toothpaste, including also specifically formulated dedicated toothpaste.

The electric power source may comprise an electric signal generator for generating an AC signal, and a control unit configured for modifying the AC signal by a predetermined control function to create the activation function of the AC signal. The power source unit may be configured to create the AC activation signal corresponding to electric current of 0.05 A to 2.0 A. The duration of the treatment session may be from 0.010 sec to 60 minutes. It should be noted that the treatment process may include a sequence of treatment session timely separated according to a predetermined time pattern.

The AC activation signal may have any suitable shape including for example sinusoidal, rectangular, triangular, saw tooth shape.

The device may include a switch configured to switch the AC activation signal ON and OFF in accordance with a treatment duration session, according to a teeth treatment protocol.

The tray unit may be configured to be a disposable unit or a reusable unit.

The electrode unit includes a predetermined number of electrodes. This may be at least one electrode, or at least one pair of electrodes. In the latter case, the electrodes of the pair may be located at the same or opposite sides of the recess in the tray. For example, at least one electrode of the electrode unit may be embedded in the tray, such that a surface of the at least one electrode is covered by a layer of material of the tray. The electrode unit may thus provide capacitive coupling between the at least one electrode and a tooth whitening paste when located in the recess. The layer of the tray covering the electrode may have a thickness in a range of 0.05 mm to 0.2 mm. In some other embodiments, each of the electrodes of the pair may have a bare metal surface. This provides for using conductive coupling between the electrodes and the whitening toothpaste.

The control unit may comprise a user interface configured for user selection of a teeth whitening program. Such program may include a predetermined number of treatment sessions, the AC activation function for each treatment session, and duration of each of the treatment sessions, as well as a time pattern for multiple treatment sessions.

The control unit may comprise a substance controller associated with a substance measurement circuit. The substance measurement circuit is located in the tray unit and is connectable to the substance controller for monitoring one or more parameters of the toothpaste being indicative of a treatment process.

Generally, the teeth whitening device may include one or more sensors for monitoring and controlling one or more conditions of the treatment process and the toothpaste material.

It should be noted that the power source unit (of AC current in the form of the activation function) may be located in a separate packaging communicating with the electrode unit of the tray through a direct electric connector, or may be connected to the electrode unit via wireless signal transmission, in which case both the power supply unit and the tray unit are equipped with corresponding communication utilities. The separate packaging with AC current source includes a built-in cable to be plugged into the tray, or a suitable connector for connection of the cable to the AC current source and to the tray. The source of AC current may include a rechargeable battery, a conventional regular battery, or AC adaptor (AC power supply) and DC to AC converter. The electrode(s) at the tray couple the AC current to the regular toothpaste by a capacitive coupling or a conductive coupling.

According to another broad aspect of the invention, there is provided a kit for use in teeth whitening treatment, the kit comprising a set comprising: at least one electric dental tray; at least one power source unit; and at least one toothpaste package; wherein the tray is configured to be applied to individual's teeth and to receive therein a sample of the toothpaste to be in contact with the teeth, and the power source unit being configured for selective electric connection with the electric dental tray to apply to an electrode unit of the tray an alternating current (AC) activation signal of a predetermined profile and maintain said AC activation signal for a predetermined duration of a treatment session, said AC activation signal having one or more frequencies in a range from a few hundreds of kHz to a few tens of MHz, thereby causing improvement of white shade grade of the teeth being in contact with the toothpaste.

According to yet another aspect of the invention, here is provided a power source unit for use with an electric dental tray for teeth whitening treatment, the power source unit comprising an electric field generator for generating AC electric signal, and a control unit connected to the electric field generator and configured for modulating the AC electric signal by a predetermined activation function, being a time and frequency function, thereby providing an AC activation signal of a predetermined profile to be applied to an electrode unit in the electric dental tray, said AC activation signal having one or more frequencies in a range from a few hundreds of kHz to a few tens of MHz.

According to yet further aspect of the invention, it provides a control unit for controlling teeth whitening treatment performed by an electric dental tray, the control unit being configured for operating an electric field generator in the tray for modulating an electric signal produced by the electric field generator by applying thereto a predetermined activation function, to thereby produce an alternating current (AC) activation signal of a predetermined profile and maintain said AC activation signal for a predetermined duration of a treatment session, said AC activation signal having one or more frequencies in a range from a few hundreds of kHz to a few tens of MHz.

In yet another aspect of the invention it provides a whitening substance for use in teeth whitening process, the whitening substance consists of a regular toothpaste carrying magnetic particles embedded therein.

The invention also provides a method of teeth whitening. The method includes: applying to at least one tooth a layer of a regular toothpaste; applying to said at least one tooth covered by the layer of the regular toothpaste an alternating electric field according to a predetermined activation function having one or more frequencies in a range from a few hundreds of kHz to a few teas of MHz; and maintaining the application of said alternating electric field for a predetermined duration of a treatment session, thereby whitening said at least one tooth.

BRIEF DESCRIPTION OF THE DRAWINGS

In order to better understand the subject matter that is disclosed herein and to exemplify how it may be carried out in practice, embodiments will now be described, by way of non-limiting example only, with reference to the accompanying drawings, in which.

DETAILED DESCRIPTION OF EMBODIMENTS

The present invention provides a novel teeth whitening device, which is advantageously configured to improve safety and reduce the cost of the teeth whitening treatment procedure, as well reduce the time it takes to achieve desirable results in a residential and professional environment. Typically, the desired results are at least those achievable with respect to teeth whitening (white shade gratin scale) in a convention professional procedure.

Teeth cleaning is a daily procedure where a toothpaste is applied with the help of a brush to the teeth in order to clean teeth, remove had odor and plaque that could be created from food residues that accumulate in the mouth. Toothpaste is a solid or gel phase of different components suspended in art aqueous phase.

Almost all commercially available types of toothpaste include a lot of similar ingredients. These ingredients could be: abrasives such as baking soda, detergents that create the foaming action associated with toothpastes use; humectants that retain moisture and prevent the toothpaste front not drying out; fluoride that maintains tooth resistance to acids and bacteria; preservative that prevent the growth of microorganisms in toothpaste; flavoring agents and sweeteners that improve the taste of toothpaste and a bleaching component that could be hydrogen peroxide, Sodium Lauryl Sulfate, hydrate silica and others.

Some of the toothpastes could include one or more coloring agents that provide the toothpaste a pleasing color and disinfectants, and mouth washes. Toothpastes have been used for many years and no adverse effects have been communicated by users of the toothpastes.

The inventor of the present invention has found that when a layer of regular toothpaste is applied to the teeth and Alternating Current (AC) is applied to the teeth covered by a layer of regular toothpaste, the application of AC current to the regular toothpaste whitens the tooth. The toothpaste could be applied to the tooth in a number of ways including use of dental tray, a brush or other paste deposition means.

Figure 1:
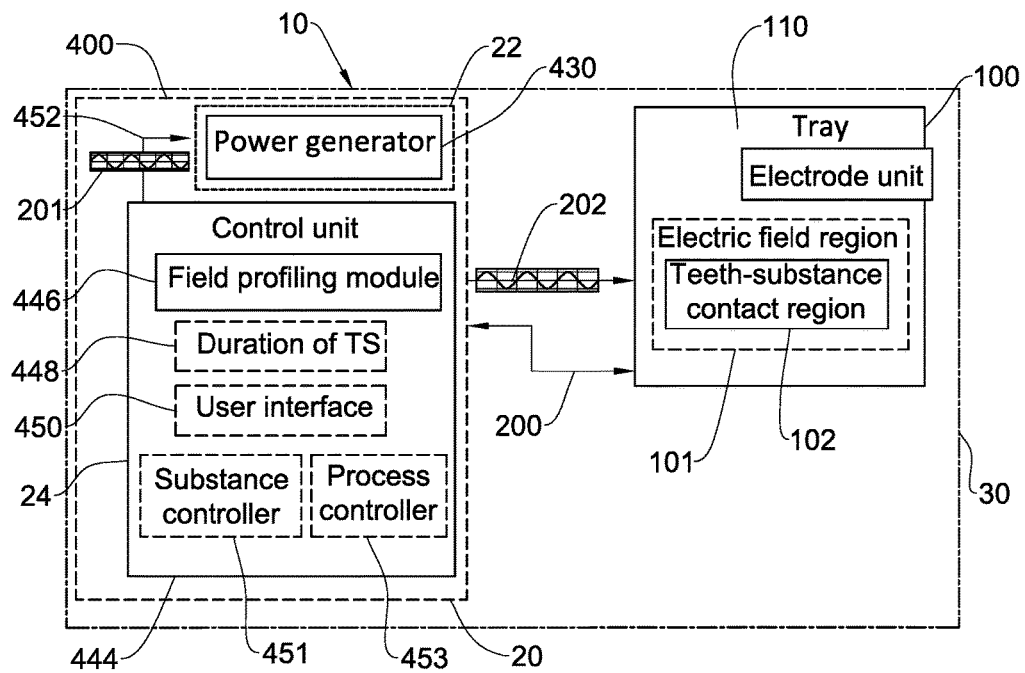
FIG. 1 is a schematic illustration of a device of the present invention.

Reference is made to FIG. 1 showing a schematic block diagram of a device 110 (medical or cosmetic) configured in accordance with the present invention. As shown in the figure, the device 10 includes a tray 100, and an electric power source device 400. The tray 100 and the electric power source device are configured for electrical connection between them, generally designated 200, which may refer to a direct electric connector 200 or a signal transmission 200. As shown in the figure by the dashed line 30, the power source device 400 may be integrated with the tray 100, being a constructional part of the tray, and being operable either using a battery or connection to a power network. As also shown in the figure as alternative option, the power source device 400 may be placed in a separate housing/package 20.

In yet another example, the elements of the power source device 400 may be distributed between the tray unit 100 and separate package 20.

The tray 100 includes an electrode unit 110, configured to be in electric communication with the electric power source unit 400, via electrical connection 200. The tray 100 is therefore at times referred to below as "electric tray". The electrode unit 110, when operated. (supplied with electric signal), creates an electric field region 101 in the vicinity thereof. It should be understood, the electrode unit may include at least one electrode, or typically at least one pair of electrodes, as will be described further below.

The tray 100 defines a cavity or a recess 102 which is configured to receive therein a whitening substance (not shown) and at least one tooth that is meant to receive treatment, such that said cavity defines a teeth-substance contact region 102. In this connection, the following should be noted: Practically, such a dental tray is configured for mounting on either the lower or upper teeth arcades. However, when a selected one or more teeth is/are to be treated the tray can be configured accordingly. In the latter case, i.e. when selected tooth/teeth is/are to be treated, the technique of the present invention advantageously allows for using the typical dental tray mountable on the entire teeth arcades because according to the invention no strong oxidizing agents are needed and therefore treatment of the selected teeth would not damage the neighboring teeth.

In the description below, the invention, and the tray configuration are exemplified as being used for applying the treatment technique to the upper and/or lower arcades. It should, however, be understood that the invention is not limited to such examples, and the principles of the invention as described herein can be easily used by a person skilled in the art for properly configuring the tray for selected at least one tooth treatment.

When the tray is mounted on the individual's teeth, the teeth and the whitening substance are in contact with each other in the teeth-substance contact region 102, and this teeth-substance contact region 102 becomes located inside the electric field region 101 thereby defining a treatment region where treatment by AC field is applied during the treatment session.

The power source 400 includes a control unit 444, and a power generator 430 which is connected to and activated by the control unit 444 via a connection circuit 452, which may be a wired or wireless connection. As shown in the figure, the power generator 430 and the control unit 444 may be joined together in a common housing/package 20, or may be placed in two separate housings 22 and 24. In some embodiments (not specifically shown), one of the power generator 430 and the control unit 444 may be integrated with the tray 100, while the other of them is left in its separate housing. It might be more practical that the power generator is integral with the electric tray, white the control unit is a separate unit which controllably modifies the electric signal generated by the power generator by a predetermined activation function and possibly its settings are updated for a specific individual (via user interface) 450. In some embodiments, the AC power generator is integral with the tray and is controlled by specially designed application for personal electronic devices, such as smartphones and tablets. To this end, the control unit is at least partially embedded in such personal electronic device.

As said, the tray 100 is configured to receive both the teeth and the whitening substance in a way that ensures an electrical contact therebetween, such that at least the whitening substance is exposed to the electric field produced by the electrode unit, which according to the invention is an alternating electric field alternating current (AC)).

As indicated above, the electrode unit 110 includes at least one electrode configured for applying the AC current to the whitening substance. In some embodiments, the electrode unit 110 may include more that one electrode, such as two or more. For example, the electrode unit 110 applies the AC current by a capacitive coupling mode, in which case the unit 110 may include at least one pair of spaced-apart electrodes with the whitening substance (and the teeth) in the space between the two electrodes. In some other examples, the AC current is produced using conductive coupling mode. More details about the different coupling modes are further detailed below with reference to FIG. 3. In some further embodiments, the electrode unit 110 may include an array of electrodes spaced by the region(s) in which the whitening substance, and possibly the teeth, is (are) situated.

The power source unit 400 is responsible for generating the electric/magnetic signals which are then transmitted (via the operation of the control unit to provide desired profile of said signals) to the electrode unit 110 in the tray, in order to generate the AC electric field/current which acts on the whitening substance (which is typically electrically conductive) and causes the bleaching of the teeth. The AC current causes an electrochemical reaction (decomposition) within the whitening substance (regular toothpaste) that breaks down the components thereof and at least one of these components causes the tooth whitening effect. For example, some bleaching ingredients of a toothpaste may be bonded to chromophores (which typically color the teeth) on the teeth and destroy the chromophores as a result of the high frequency AC current (i.e. that changes its direction very rapidly, e.g. few millions times per second). As indicated above, the regular toothpaste may comprise magnetic particles embedded therein. In this case, application of alternating magnetic field of a desired profile results in a corresponding motion pattern of the magnetic particles in the toothpaste. This motion has rapidly varying motion vector affecting interaction between the ingredients of the toothpaste and the teeth resulting in the teeth whitening.

As briefly described above, the power source 400 includes the power generator 430 which physically generates the electric/magnetic field/signals modified by the activation function produced by the control unit 444.

To this end, the control unit 444 is typically a computerized system being a hardware and/or software based system, and includes at least such as modules as a field profiling module 446, a duration controlling module 448 for controlling duration of a treatment session, and a user interface module 450. In some embodiments, the control unit 444 also includes a substance controller 451, configured for measuring/monitoring one or more parameters of the whitening substance (material status), which may be indicative of the treatment process, such as for example measurement of impedance of the of the whitening substance, as will be described further below. The substance controller is actually associated with a measurement/sensing circuit (electric, optical, electro-optical, etc.), which is typically integral with the tray and connectable (via wires or wireless) to the substrate controller 451.

Also, as shown in the figure, the control unit may also include a process controller 453 for controlling various parameters and conditions of the treatment (whitening) process, such as one of the following: control the amount and location of the toothpaste, custom formulated whitening substance within the tray recess or channel. As will be described further below, the power source unit may include one or more indicators which is/are associated with one or more sensor(s) and controller(s) to provide indication and alert the user if the whitening process deviates from the treatment plan/program.

The field profiling module 446 generates a control function (shown at 201) which is a time and frequency function and controls the profile/shape (the frequency and amplitude over time) of the electric/magnetic field/signals to form a desired AC electric activation function 202. The control function (shown at 201) may be applied to the output of the power generator 430 (or may be fed into the power generator) in order to properly modify the electric/magnetic field activating signal. It should be understood that in case the power generator is configured to be directly connected to a power network, the power generator or the control unit (as the case may be) includes an AC-DC converter and a DC-AC converter (as well as A-to-D converter). If the power generator includes a battery, then either the power generator or the control unit includes an appropriate DC-AC converter.

Generally, the parameters of the control function and accordingly of the activation function (shape, frequency and amplitude) may be of any suitable shape or magnitude. For example, the shape of the activation function may be one or a combination of sinusoidal, rectangular, triangular, saw tooth or any other suitable shape. Preferably, the frequency of the electric signal is relatively high, e.g. of a few hundreds of kHz and up to the range of MHz. The amplitude may be in the range from 3 Vrms up to 50 Vrms. The activation function may also be a combination of different activation sub-functions (via multiplexing or any other combining method known in the art). In other words, the treatment protocol may include application of a generated alternating electric field which has a single shape and a single frequency for the whole duration of activation, or it may have a consequence of shapes and frequencies.

The control unit 444 also controls the duration of the treatment session via the module 448, and possibly also a time pattern of multiple treatment sessions, which may be similar or different in the duration times and/or activation functions produced by the module 446.

Finally, the control unit also includes a suitable user interface 450 which enables the user to control the whole treatment session, by defining each of the parameters of the activation function and its duration.

Thus the device of the present invention provides full control over all the parameters needed to execute a successful and effective teeth whitening treatment. The full or partial control of the treatment process parameters (including also a treatment session duration, number of treatment sessions, the time pattern of the multiple treatment sessions, etc.) may be setup in the control unit prior to supplying the device, or only the control unit, to the user, and/or may give the user access for updating/adjusting the parameter(s).

The above described device may be supplied in a specific kit for use in teeth whitening treatment (professional or home use). The kit includes a set of one or more electric dental trays, one or more power source units, and one or more toothpaste packages. The toothpaste package includes a regular toothpaste, e.g. toothpaste containing whitening agent(s); or toothpaste (with or without whitening agents) containing magnetic particles therein; or toothpaste (with or without whitening agents, and with or without magnetic particles) containing or accompanied with hyaluronic acid.

Figure 2:
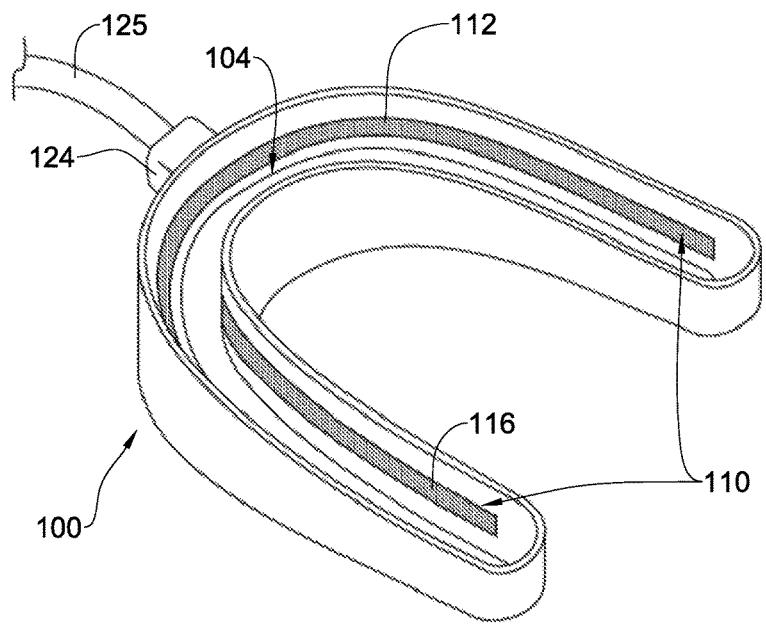
FIG. 2 is an example of a tray used in present tooth whitening device.

Reference is now made to FIG. 2 illustrating a specific but not limiting example of a dental tray 100 which may be included in present tooth whitening device. Tooth tray 100 could be constructed to fit the respective upper and/or lower sets or arcades of teeth in the user's mouth. Tooth tray 100 may be of a conventional design including a recess or channel 104 the width and depth of which could be produced in a number of sizes to achieve compliance with anatomical features of different users and compliance with the teeth. The recess or channel 104 is also configured to retain the whitening material against the teeth to be whitened. As indicated above, the whitening material is a regular toothpaste. Tray 100 further includes an electrode unit 110 which includes a pair of electrodes 112 and 116. Electrodes 112 and 116 could be attached to, or in the form of coatings on, or be embedded in walls of tray 100. The electrodes may be unitary electrodes that follow the contour of tray 100 at least within a part of the recess 104, or may be segmented electrodes, i.e. composed of a number of electrode segments following the contour of at least a part of the tray walls. Electrodes 112 and 116 receive AC current activating field (202 in FIG. 1) from the power source unit 400, which may be located outside the tray 100 and connected to die tray 100 (the electrode unit) with the help of a connector 124, or may be at least partially located within the connector 124. In the latter case, the configuration may be such that the connector 124 includes the control unit (444 in FIG. 1) and the power generator (430 in FIG. 1) which is in turn connectable to a power network via a wire 125; or the connector may include the power generator (e.g. equipped with battery or connectable to the power network) which is connectable to the external control unit e.g. via wired connection 125. In some examples, a thermistor could be provided in (attachable to) the tray to monitor the teeth whitening process temperature. Such temperature could typically vary from 40 degrees C. to 48 degrees C.

Figure 3:
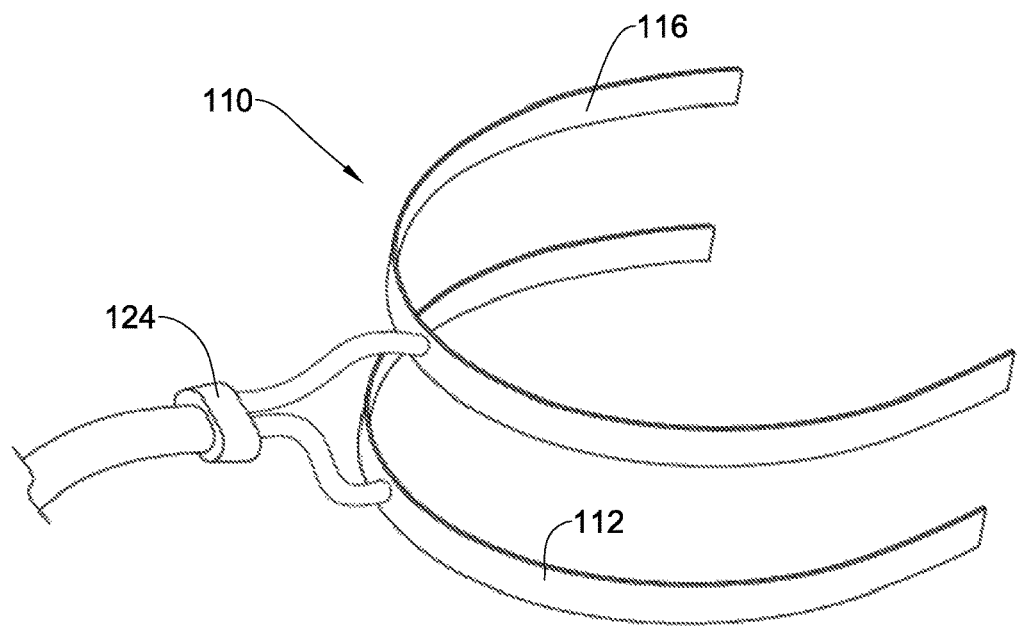
FIG. 3 is an example of AC electrodes embedded in the tray used in present tooth whitening method.

FIG. 3 shows a non-limiting example of the configuration of the electrode unit 110. The electrode unit includes a pair of AC electrodes 112 and 116 which may be embedded in the tray 100. Electrodes 112 and 116 could be configured to couple to the whitening toothpaste in a capacitive or conductive/resistive coupling mode. For coupling to the toothpaste in a capacitive mode, at least one of the electrodes 112 and 116 may be covered by a dielectric layer/coating. For example, the electrode being embedded into the tray becomes covered by a layer of tray material, thus, when operated by electric signal, create capacitive coupling with the toothpaste. The thickness of the layer of tray material could be between 0.05 mm to 0.2 mm. For coupling to the toothpaste in a conductive or resistive mode electrodes 112 and 116 surface could be a bare metal surface. Electrodes 112 and 116 are made of stainless steel, titanium, gold or other bio-compatible current conductive material and do not need to be covered by a layer of tray material. Tray 100 is unitary tray that could be formed of silicone or foam material. Tray 100 could be made sufficiently stiff to receive and hold the regular toothpaste.

As already noted, the shape of the tray generally conforms to the arrangement of upper and lower teeth in a treated person jaw. FIG. 2 provides an example of tray suitable for use for whitening of one set of teeth. It could be the upper or lower set of teeth.

Figure 4:
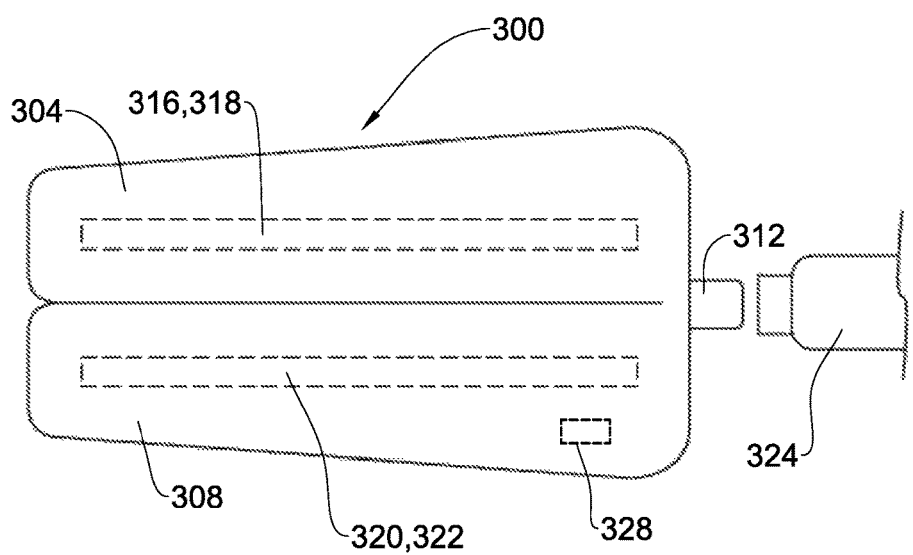
FIG. 4 is an example of a tray used in present tooth whitening method for concurrent whitening of the upper and lower teeth set.

FIG. 4 is an example of a tray device 300 configured for concurrent whitening of the upper and lower teeth set. Tray 300 could be produced as a single unitary tray including upper and lower integrally made trays 304 and 308 each defining the respective recess for the teeth-whitening substance contacting region. The upper and lower parts 304 and 308 of the tray could be fastened to each other by any known in the art technique. Alternatively, two separate trays 304 and 308 can form a common tray device 300. Irrespectively of whether the trays 304 and 308 are integral or separate structures, each of the trays 304 and 308 is includes its electrode unit to apply AC activation field to the respective electric field region in the recess. In the present not limiting example, the trays 304 and 308 carry electrode pairs 316, 318 and 320, 322. A connector 312 is provided which may be configured as described above (i.e. connect the tray to the power source unit or include the entire power source unit or a part thereof). The connector 312 may also be configured to receive a handle 324 supporting convenient handling of the tray device 300. In some embodiments, a thermistor 328 could be embedded in/attached to the tray(s) to monitor the teeth whitening process temperature (that could vary from 40 degrees C. to 48 degrees C.).

Figure 5:
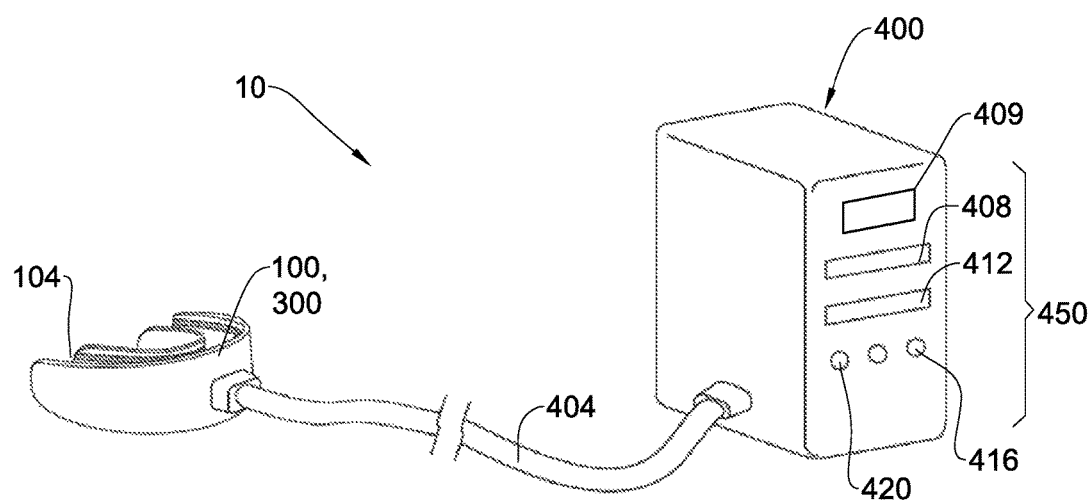
FIG. 5 is an example of a power supply and control unit for use with the tooth whitening device.

Reference is made to FIG. 5 exemplifying the device 10 of the present invention. In this specific not limiting example, the AC power source 400 is located in a separate housing connectable to the tray unit 100 (or 300). A cable 404 could be used to connect between input and output ports of the tray unit 100 and the power supply source unit 400 for supplying to the teeth-substance contact region 104 the AC current field in the form of the activation function having predetermined profile, preferably of substantially high frequency(cies), as described above. It should, however, be understood that instead of the cable 404, a wireless connection could be established. In this case, both the tray unit 100 (its electrode unit) and the power supply source unit 400 include appropriate communication utilities. This technique of wireless communication is generally known and therefore should not be described in details, except to note that the communication may be of RF, IR, microwave and/or acoustic communication type. The control unit (software and/or hardware) installed in the power source unit may include a user interface 450 including a display 409, as well as some control knobs or switches 408-412 that support setting one or more of teeth whitening treatment process parameters, such as treatment session duration and possibly also a number of treatment sessions and a time pattern thereof, and the profile (magnitude, frequency and shape) of the AC field/current, as can be controlled by the control unit (modules 446 and 450 of FIG. 1), and some other indicators on the treatment process, for example such as the temperature in the mouth cavity. There can also be one or more indicators 416-420 (e.g. color indicators) to indicate the operational condition as well as working temperature of the device. For example, one color can be provided to indicate that the process progresses normally, a second color can be shown to indicate that the temperature inside the mouth is not sufficient for the teeth whitening treatment, and a third color can be used to indicate that the temperature is approaching the allowed upper limit. Additionally or alternatively, one or more indicators (color indicators) can be provided as one or more windows provided on the exterior of the tray unit 100 or 300. It should be understood that the invention is not limited to any of these examples, and the indication if used, may be via the display 409 (which may be any suitable display including but not limited to TFT, LCD, OLED display e.g. with touch panel), as well as may include sound indicator(s).

Preferably, AC current frequency, controlled by the module 446 of the control unit 444, could be in the range from 300.0 kHz to 40.0 MHz. Typically, AC current frequency is from 1.0 MHz to 10.0 MHz or from 0.5 MHz to 8.0 MHz. The AC current supplied could typically be between 0.005 amp to 1.0 amp, alternatively the AC current could be between 0.05 amp to 0.5 amp. It should be understood that the treatment session duration depends on many factors including such as the initial condition of the individual's teeth and the AC signal. However, the inventors have shown that the duration of a treatment session performed by the technique of the invention may be less than a second (e.g. 10 milliseconds), and generally may not exceed half an hour.

The power source unit 400 may be configured to supply AC current for a time of 0.010 sec to 30 min (duration of a treatment session). The AC power could be in the range from 0.005 W to 5.0 W. Typically, the range of the RF power is from 0.05 W to 3.0 W and it could be coupled into the regular toothpaste in a pulsed or continuous delivery mode of the AC current. During course of the teeth whitening procedure, AC current could heat the toothpaste and the mouth cavity of the user or patient to a temperature of 40 degrees C. to 48 degrees C.

It should be noted that simple heating of the toothpaste and application of the heated toothpaste to the teeth does not cause any tooth whitening effect, but when combined/caused by application of the AC current/field of a predetermined profile, it provides the fast and effective teeth whitening effect.

For teeth whitening or bleaching a user could fill the tray 100 or 300 by regular commercially available toothpaste, grip the distal end of a device handle (324 in FIG. 4) and insert the tray into his mouth. Channel(s) or recess(es) 104, while serving as the teeth-substance contact region(s), also prevent(s) the tray(s) from accidentally shifting in the mouth. The user or patient could also squeeze the sides of the tray together by closing his mouth and producing a bite like movement by his teeth. The user further can switch ON the AC current field supply and set the timer to start the teeth whitening treatment session.

As indicated above, the teeth whitening treatment induced by the application of AC field of the desired profile affects a corresponding heating profile in the treatment region and causes electrochemical reaction of decomposition of the "regular tooth paste" that breaks down the components of the "regular tooth paste" causing the tooth whitening effect. The alternating current might also affect additional tooth paste ingredients that catalyze the teeth bleaching process reaction.

In the following, some experimental data acquired by the inventor is shown. The tests were performed on fifteen extracted teeth using a number of commercially available, regular tooth cleaning pastes: Colgate Max White One, Colgate Total, Aquafresh Fresh, Colgate Max Fresh, Oral B Proexpert, Arm & Hammer Advanced White, Aquafresh Extreme Clean Pure, Sensodyne Repair & Protect Toothpaste, Sensodyne Pronamel Toothpaste, Arm & Hammer Enamel Pro Repair Sensitive, Oral B 123 Paste, Oral B Proexpert All Around, Oral B Paste Complete Extra Fresh.

"Effectiveness" of a teeth whitening could be characterized by a number of parameters. For example, (a) number of shades removed or shade achieved in one treatment, time required by a single treatment or even by a number of treatments to achieve the desired tooth shade, duration of the teeth whitening effect. Effectiveness of the treatment could be measured in absolute terms, for example, the change in the number of shades as compared to standard existing teeth whitening techniques or in relative terms, for example by comparison with an untreated control tooth.

Tooth shade, as used in the current disclosure, means a scale according the whiteness and brightness of a tooth could be classified. Tooth shades vary from very light to very dark. There is no established tooth shade standard and each manufacturer of dental prosthetic materials provides its own scale. Some scales could have 16 tooth shades other tooth shade scales could have more than 30 tooth shades. Recently, tooth bleached shades have been developed, for example Vita Bleacheguide 3D-MASTER by VITA Zahnfabrik H. Rauter GmbH & Co. KG D-79713 Bad Sackingen Germany. These scales allow establishing a desired tooth whitening shade or result.

Figure 6:
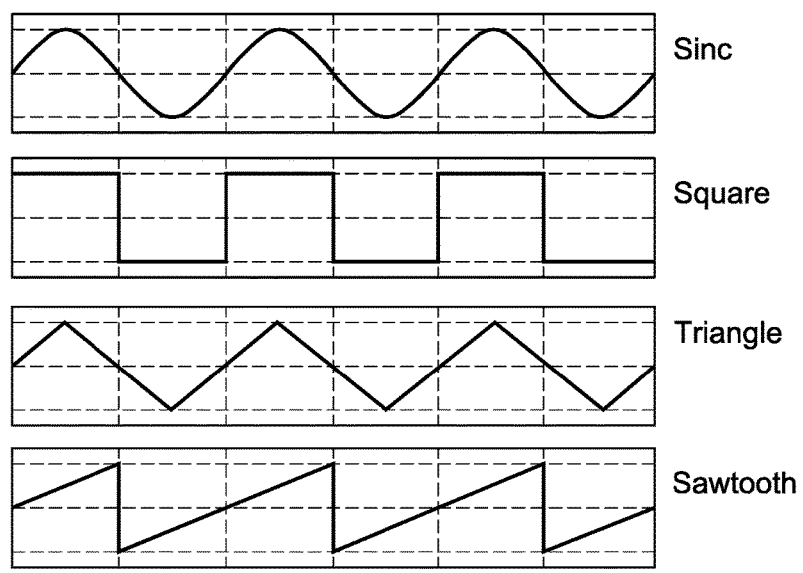
FIG. 6 is an example of AC currents used in several experiments, the results of which are presented in the application.

FIG. 6 is an example of suitable AC current profiles used in the tests presented in the current application.

The present teeth whitening process among others was controlled using the tooth paste or custom formulated material impedance. As known, impedance (Z) means the opposition that an electronic component, circuit, or system offers to alternating current (i.e., similar to resistance in direct current scheme). Measurement of impedance supports control and variation of treatment time, treatment process, temperature change, applied AC current and AC current application duty cycle.

The device is also configured to control the amount and location of the tooth paste and/or custom formulated whitening material within the tray recess or channel 104, and alert the user if the (whitening) material fills-in proper recess or channel 104 and the circuit between electrodes 112 and 116 contains a sufficient amount of the whitening material. In addition, the device supports generation of information related to the whitening material identification. The device includes a look-up-table where information on a number of used materials could be recorded. Upon identification of the material an optimal treatment process parameters could be set.

The following Table 1 summarizes the test results.

TABLE 1

| Tooth # | Initial Shade value | Toothpaste | Whitening parameters | Post whitening Shade value |
|---|---|---|---|---|
| 1 | C4 | Colgate Max White One | Electrical Current 250 mA$_{RMS}$, 20 minutes; temperature between 42-45° C. | B2 |
| 2 | D4 | Colgate Max White One | Electrical Current 250 mA$_{RMS}$, 20 minutes | C2 |
| 3 | C3 | Colgate Max White One | Electrical Current 0 mA$_{RMS}$, 20 minutes; temperature between 42-45° C., No electrical current, the toothpaste was heated in "bain-marie". | C3 |
| 4 | A3 | Colgate Optic White | Current 250 mA$_{RMS}$, 20 minutes; temperature between 42-45° C. | B1 |
| 5 | C4 | Colgate Optic White | Current 250 mA$_{RMS}$, 20 minutes; temperature between 42-45° C. | D3 |
| 6 | C2 | Colgate MaxWhite WITH MICRO-CRYSTALS | Current 250 mA$_{RMS}$, 20 minutes; temperature between 42-45° C. | C2 |
| 7 | B2 | Aquafresh MULTI-ACTION + WHITENING | Current 250 mA$_{RMS}$, 20 minutes; temperature between 42-45° C. | B1 |
| 8 | C2 | Aquafresh MULTI-ACTION + WHITENING | Current 250 mA$_{RMS}$, 20 minutes; temperature between 42-45° C. | C1 |
| 9 | B3 | Oral-B complete | Current 250 mA$_{RMS}$, 20 minutes; temperature between 42-45° C. | B2 |

Tooth shades assessment and tooth whitening results comparison was made using VITAPAN classical shade guide.

The device is able to measure the Toothpaste or/and Peroxide or/and any whitening compounds electrical parameters like: impedance and current through the compound.

The present invention has proved to be substantially better than the existing tooth whitening techniques: the cost of a regular commercially available toothpaste is substantially lower than the cost of special tooth whitening gels; the treatment time of a single session is five to twenty five minutes and is substantially shorter than the treatment time by the existing gels accompanied by DC current or LEDs light, which is usually 20 to 60 minutes for a single session. The number of shades whitened at a single teeth whitening session varied from two to seven shades. A single teeth whitening session has been required to reach tooth whitening results similar to the results achieved by six to tell sessions using the existing tooth whitening gels accompanied by DC current and/or LEDs illumination.

The inventor does not exclude that further improvement of teeth whitening results could be achieved by specially formulated toothpaste. For example, the inventor used a custom made paste and obtained sufficient teeth whitening results.

Another advantage of the present invention is that the existing tooth pastes do not contain hydrogen peroxide $H_2O_2$. The use of $H_2O_2$ in most countries in the World, except the U.S.A., for consumer products is limited to 0.1%, which is not enough for teeth whitening effect by existing in-office or home tooth whitening methods. There is no need prior to applying a regular existing tooth paste to isolate the user or patient's teeth, since the existing toothpastes do not cause any damage to the gingival tissue.

What is claimed is:

1. A teeth whitening device comprising a tray unit and an electric power source unit;

said tray unit comprising:

a whitening substance that is free of hydrogen peroxide and contains a conductive substance;

at least one dental tray comprising a recess configured for receiving therein at least one tooth of a dental arcade and for holding a layer of said whitening substance such that said at least one tooth is covered by said layer of the whitening substance, thereby defining a teeth-substance contact region in said recess;

an electrode unit extending along at least part of said recess and configured and operable for creating an alternating current (AC) activation signal within said recess that acts on said whitening substance to thereby apply a treatment session to said at least one tooth being covered with the layer of said whitening substance during the treatment session; and a substance measurement circuit comprising a sensing circuit of one or more of the following kinds: electric, optical and electro-optical;

said electric power source unit comprising:

an electric signal generator configured and operable for generating an alternating current (AC) signal and controllably applying said AC activation signal corresponding to electric current of 0.05 A to 2.0 A to said electrode unit during the treatment session; and a control unit configured for modifying said AC signal of the electric signal generator to create said AC activation signal, said control unit comprising a substance controller associated with said substance measurement circuit, said substance measurement circuit being connectable to said substance controller, said substance controller being designed to monitor impedance of said whitening substance inside the tray unit;

wherein:

said AC activation signal is a high frequency signal in a range of 1 Mhz to 10 MHz; such that said high frequency signal breaks down and/or activates one or more components of said whitening substance, and causes a rapidly varying motion of one or more of said components of the whitening substance that affect interaction between the one or more components of the whitening substance and the at least one tooth covered by the layer of the whitening substance, and cause(s) improvement of white shade grade of said at least one tooth being covered by said whitening substance.

2. The teeth whitening device according to claim 1, wherein the power source unit is configured to maintain the AC activation signal for a treatment session duration of 0.010 sec to 60 minutes.

3. The teeth whitening device according to claim 1, wherein said AC activation signal has one of the following shapes: sinusoidal, rectangular, triangular, saw tooth.

4. The teeth whitening device according to claim 1, further comprising a switch configured to switch ON and OFF said AC activation signal in accordance with a duration of the treatment session according to a teeth treatment protocol.

5. The teeth whitening device according to claim 1, wherein the tray unit is configured to be a disposable unit.

6. The teeth whitening device according to claim 1, wherein the electrode unit comprises a predetermined number of electrodes.

7. The teeth whitening device according to claim 6, wherein at least one electrode of the electrode unit is embedded in the tray, such that a surface of said at least one electrode is covered by a layer of material of the tray.

8. The teeth whitening device according to claim 7, wherein said electrode unit is configured for providing capacitive coupling between said at least one electrode and the tooth whitening substance when located in said recess.

9. The teeth whitening device according to claim 1, wherein each of the electrodes of the pair has a bare metal surface.

10. The teeth whitening device according to claim 9, wherein said electrode unit is configured for providing conductive coupling between the electrodes and whitening toothpaste.

11. The teeth whitening device according to claim 1, wherein the control unit comprises a user interface configured for user selection of a teeth whitening program.

12. The teeth whitening device according to claim 1, further comprising one or more sensors for monitoring and controlling one or more conditions of the treatment process and the whitening substance.

13. The teeth whitening device according to claim 1, wherein said whitening substance carries magnetic particles embedded therein.

14. The teeth whitening device according to claim 1, wherein said whitening substance comprises hyaluronic acid.

* * * * *